US008703102B2

(12) United States Patent
Kalechofsky et al.

(10) Patent No.: US 8,703,102 B2
(45) Date of Patent: Apr. 22, 2014

(54) SYSTEMS AND METHODS FOR PRODUCING HYPERPOLARIZED MATERIALS AND MIXTURES THEREOF

(75) Inventors: Neal Kalechofsky, Stow, MA (US); Avrum Belzer, Brookline, MA (US)

(73) Assignee: Millikelvin Technologies LLC, Braintree, MA (US)

( * ) Notice: Subject to any disclaimer, the term of this patent is extended or adjusted under 35 U.S.C. 154(b) by 0 days.

(21) Appl. No.: 12/879,634

(22) Filed: Sep. 10, 2010

(65) Prior Publication Data

US 2011/0062392 A1   Mar. 17, 2011

Related U.S. Application Data

(63) Continuation of application No. PCT/US2010/047310, filed on Aug. 31, 2010, and a continuation-in-part of application No. PCT/US2009/039696, filed on Apr. 6, 2009.

(60) Provisional application No. 61/238,647, filed on Aug. 31, 2009, provisional application No. 61/042,398, filed on Apr. 4, 2008, provisional application No. 61/111,050, filed on Nov. 4, 2008.

(51) Int. Cl.
*A61B 5/055* (2006.01)
*A61K 49/06* (2006.01)
*G01N 24/00* (2006.01)
*G01R 33/20* (2006.01)

(52) U.S. Cl.
USPC ............. 424/9.3; 62/51.1; 560/231; 562/607; 600/410

(58) Field of Classification Search
None
See application file for complete search history.

(56) References Cited

U.S. PATENT DOCUMENTS

| | | | |
|---|---|---|---|
| 5,545,396 A | 8/1996 | Albert et al. | |
| 5,617,859 A | 4/1997 | Souza et al. | |
| 6,453,188 B1 | 9/2002 | Ardenkjaer-Larsen et al. | |
| 6,466,814 B1 * | 10/2002 | Ardenkjaer-Larsen et al. | 600/420 |
| 6,651,459 B2 | 11/2003 | Kalechofsky | |
| 2003/0017110 A1 * | 1/2003 | Pines et al. | 424/9.6 |
| 2004/0066193 A1 | 4/2004 | Ardenkjaer-Larsen et al. | |
| 2005/0200356 A1 | 9/2005 | Hennig | |
| 2006/0124510 A1 | 6/2006 | Kalechofsky | |
| 2006/0173282 A1 | 8/2006 | Ardenkjaer-Larsen et al. | |
| 2007/0156046 A1 | 7/2007 | Hasing et al. | |
| 2008/0000471 A1 | 1/2008 | Bolam et al. | |

FOREIGN PATENT DOCUMENTS

| | | |
|---|---|---|
| WO | WO-91/12024 | 8/1991 |
| WO | WO-95/27438 | 10/1995 |
| WO | WO-96/40585 | 12/1996 |
| WO | WO-97/37177 | 10/1997 |
| WO | WO-97/37178 | 10/1997 |
| WO | WO-98/01766 | 1/1998 |
| WO | WO-98/58272 | 12/1998 |
| WO | WO-99/07415 | 2/1999 |
| WO | WO-99/24080 | 5/1999 |
| WO | WO-99/34189 | 7/1999 |
| WO | WO-99/35508 | 7/1999 |
| WO | WO-99/66254 | 12/1999 |
| WO | WO-01/11285 | 2/2001 |
| WO | WO-02/36005 | 5/2002 |
| WO | WO-02/37132 | 5/2002 |
| WO | WO-2006/079702 | 8/2006 |
| WO | WO 2007007022 A1 * | 1/2007 |
| WO | WO-2007/136439 | 11/2007 |
| WO | WO-2007136439 A2 | 11/2007 |
| WO | WO-2007136439 A3 | 11/2007 |
| WO | WO-2009/146153 | 12/2009 |
| WO | WO2011026103 | 3/2011 |

OTHER PUBLICATIONS

N Nirmala, G Wagner. "Measurement of 13C Spin-Spin Relaxation Times by Two-Dimensional Heteronuclear 1 H-13C Correlation Spectroscopy." Journal of Magnetic Resonance, vol. 82, 1989, pp. 659-661.*
PhysicalGeography.net Fundamentals eBook. "Chapter 7: Introduction to the Atmosphere." http://www.physicalgeography.net/fundamentals/7a.html (accessed Oct. 18, 2011). Publication Date Unknown, 3 printed pages.*
CN—Office Action—200780011444.3, Chinese Office Action dated Aug. 30, 2010 (6 pgs.).
CN—Office Action—200780011444.3, English Translation of Chinese Office Action dated Aug. 30, 2010 (4pgs.).
International Preliminary Report on Patentability for PCT/US2009/039696 together with the Written Opinion of the International Searching Authority (ISA) dated Nov. 17, 2009 (7 pages).
CN—200780011444.3—Office Action, Aug. 30, 2010, Kalechofsky.
CN—200780011444.3—English Translation of Office Action, Aug. 30, 2010, Kalechofsky.
International Search Report for Application No. PCT/US2010/047310, Mar. 3, 2011.
Research News Berkeley Lab; Hyper-Crest MRI Breaks New Ground in Molecular Imaging, Oct. 19, 2006.
APS Water Presentation; Mar. 5-9, 2007, Denver; http://www.aps.org/meetings/march.
International Search Report and the Written Opinion of the International Searching Authority dated Nov. 17, 2009.
"Enhancement of Solution NMR and MRI with Laser-Polarized Xenon," Navon, G., Song, Y.-Q., Rõõm, T., Appelt, S., Taylor, R. E. and Pines, A., (1996). Science 271, 1848.
"Polarization Transfer using Hyperpolarized Supercritical Xenon," Jason C. Leawoods, Brian T. Saam, and Mark S. Conradi, Chem. Phys. Lett. 327, 359-364 (2000).

(Continued)

*Primary Examiner* — Frederick Krass
*Assistant Examiner* — Isaac Shomer
(74) *Attorney, Agent, or Firm* — Day Pitney LLP; Brian R. Pollack

(57) ABSTRACT

The present disclosure provides various methods and systems for manufacture, transport and delivery of material including highly polarized nuclei that is in a hyperpolarized state.

23 Claims, 2 Drawing Sheets

(56) References Cited

OTHER PUBLICATIONS

"Increase in signal-to-noise ratio of > 10,000 times in liquid-state NMR" Jan H. Ardenkjwr-Larsen, Björn Fridlund, Andreas Gram, Georg Hansson, Lennart Hansson, Mathilde H. Lerche, Rolf Servin, Mikkel Thaning, and Klaes Golman, Proc Natl Acad Sci U S A. Sep. 2, 2003; 100(18): 10158-10163.

"Polarization of $^3$He, $D_2$ (and possibly $^{129}$Xe) using cryogenic techniques" G. Frossati, Nuclear Instruments and Methods in Physics Research Section A: Accelerators, Spectrometers, Detectors and Associated Equipment; vol. 402, Issues 2-3, Jan. 11, 1998, pp. 479-483.

"In vivo magnetic vascular imaging using laser-polarized 3He microbubbles" Mark S. Chawla, X. Josette Chen, Harald E. Moller, Gary P. Cofer, C. Ted Wheeler, Laurence W. Hedlund, and G. Allan Johnson, Proc. Natl. Acad. Sci. USA vol. 95, pp. 10832-10835, Sep. 1998 Medical Sciences.

International Search Report and the Written Opinion of the International Searching Authority dated Jul. 7, 2008 for PCT/US2007/004654.

International Preliminary Report on Patentability for PCT/US2007/00465, Jul. 7, 2008.

* cited by examiner

SYSTEMS AND METHODS FOR PRODUCING HYPERPOLARIZED MATERIALS AND MIXTURES THEREOF

CROSS-REFERENCE TO RELATED APPLICATIONS

This application is a continuation of and claims the benefit of priority of International Application No. PCT/US2010/47310, filed Aug. 31, 2010, which in turn claims the benefit of priority to U.S. Provisional Patent Application Ser. No. 61/238,647, filed Aug. 31, 2009. This application is a continuation in part of and claims the benefit of priority of International Application No. PCT/US2009/39696, filed Apr. 6, 2009, which in turn claims the benefit of priority of U.S. Provisional Patent Application Ser. No. 61/042,398, filed Apr. 4, 2008 and U.S. Provisional Patent Application Ser. No. 61/111,050, filed Nov. 4, 2008. This application is also related to U.S. Provisional Patent Application Ser. No. 60/775,196 filed Feb. 21, 2006, U.S. Provisional Patent Application Ser. No. 60/802,699 filed May 23, 2006, U.S. Provisional Patent Application Ser. No. 61/042,239 filed Apr. 3, 2008 and U.S. patent application Ser. No. 12/193,536, filed Aug. 18, 2008. The disclosure of each of the aforementioned patent applications is incorporated by reference herein in its entirety.

BACKGROUND

1. Field of the Disclosure

The present disclosure relates to improved materials including hyperpolarized nuclei and techniques for making the same.

2. Description of Related Art

Recent experiments have demonstrated that hyperpolarization of various nuclei can survive the transition from one molecule to another that takes place during a chemical reaction. For example, it has been shown that hyperpolarized ("HP") $^{13}C$ nuclei in sodium pyruvate can be metabolized by cancerous tissue and produce HP lactate, alanine and the like.

A further example can be found in the production of HP fumarate, which can be manufactured by first hyperpolarizing nuclei in fumaric acid and then allowing the acid to react with a base solution to form HP fumarate. HP sodium pyruvate (i.e., sodium pyruvate including hyperpolarized nuclei) may be manufactured in a similar fashion. In reactions such as these the amount of polarization lost during the chemical reaction has been shown to be small.

These are examples of chemical reactions in which at least one precursor molecule in the chemical reaction is hyperpolarized so that at least one of the end products of the chemical reaction is in turn hyperpolarized.

In each of the aforementioned examples, Dynamic Nuclear Polarization (DNP) was used to hyperpolarize the precursor molecule. In this process, the molecule to be hyperpolarized is mixed with a polarization agent containing a source of free electrons, typically a trityl radical (TA). In some instances an electron paramagnetic agent (EPA) may be used in conjunction with the TA or by itself.

This method of hyperpolarization is problematic for in vivo applications, as the TA/EPA is strongly contraindicated for in vivo applications. The TA/EPA must then be stringently removed prior to injection of the HP material. However, the level of polarization in the HP material that survives after filtration of the TA/EPA is not presently clear. Moreover, safe levels of exposure to small amounts of TA/EPA have not been established by the FDA. Furthermore, use of this technique is not amenable to the ready transport or storage of hyperpolarized material.

Very high nuclear polarizations can be produced in materials containing nuclei with non zero spin using a variety of methods well known in the art. The simplest of these is to subject the material to very high magnetic fields (typically, B>10 T) and very low temperatures (typically, T<100 mK) where the saturated nuclear polarization of any non zero spin nuclei is very high.

Unfortunately, under such conditions, the relaxation time of most nuclei is extremely long because at low temperatures, molecular motion, which is a major source of nuclear magnetic relaxation, is greatly diminished. To address this drawback, a variety of relaxation agents have been used to reduce $T_1$ in the high B/T environment including dysposium, gadolinium, oxygen and others.

An alternative to employing a relaxation agent is to incorporate a polarization agent such as a trityl radical and then transfer polarization from the agent to nuclei in the target material. This approach has the advantage of not requiring such low temperatures or high fields and has been used to demonstrably produce very large polarizations in small amounts of material. It has become the basis of a commercially available research device with the trade name Hypersense®.

However, admixture of either an external relaxation agent or a polarization agent has a number of drawbacks. First off, they are generally equally effective at depolarizing the material while still in the solid state upon removal from the high B/T environment. This makes it very difficult to store/transport the hyperpolarized material any significant distance from the polarizer and therefore mandates that the polarizer be placed very close to the MR machine in which the study utilizing hyperpolarized material is to be carried out. Secondly, most relaxation or polarizations agents are frequently toxic. This makes such agents problematic for use in in vivo MR studies.

For this reason alternative relaxation agents that are non toxic and can furthermore be removed without depolarizing the material have been developed. For example, U.S. Pat. No. 6,651,459 teaches the use of $^3He$ as a relaxation agent by adsorbing layers of $^3He$ on a high surface area substrate constructed from the material to be hyperpolarized. Quantum tunneling in the $^3He$ overlayers causes rapid relaxation in the underlying material leading to rapid saturation of the nuclear polarization in a high B/T environment. $^3He$ is chemically inert and can moreover be thoroughly removed from the material prior to warm up from a high B/T environment which addresses in vivo usage concerns. U.S. Pat. No. 6,651,459 further teaches the use of $^4He$ to remove the $^3He$ from the surface of the polarized material to minimize depolarization upon warmup.

An aspect of the above process is that the $^3He$ can only effectively relax the substrate layer with which it is in intimate contact. Thus, the material must be made into a very high surface area substrate prior to polarization which may impose material handling difficulties.

There is therefore a need in the art for a methods of manufacturing hyperpolarized ("HP") material where the material is not mixed with any kind of external relaxation or polarization agent. More generally, there remains a need in the art for improved approaches to manufacture, transport and use of highly polarized materials. The present disclosure provides a solution for these problems.

SUMMARY OF THE DISCLOSURE

Advantages of the present disclosure will be set forth in and become apparent from the description that follows. Additional advantages of the disclosure will be realized and attained by the methods and systems particularly pointed out in the written description and claims hereof, as well as from the appended drawings.

To achieve these and other advantages and in accordance with the purpose of the disclosure, as embodied herein, in one embodiment, the disclosure provides a method of producing a material containing hyperpolarized nuclei. The method includes formatting a first material into a high surface area configuration. Next, in a polarizing cryostat, the first material is exposed to $^3$He at a temperature below about 10K and a magnetic field in a manner sufficient to substantially increase the polarization of at least one nuclei in the first material. The temperature of the first material is then increased without melting or sublimating the first material resulting in nuclei in the first material becoming hyperpolarized. If desired, the first material is then reacted with at least one other material to form a mixture including hyperpolarized nuclei.

In further accordance with the invention, the mixture may be a solution. If desired, the first material may be melted prior to, or as a part of, the reacting step. The first material may be exposed to $^4$He after exposing the first material to $^3$He. If desired, the first material may be stored in a hyperpolarized condition in a separate cryostat. The first material may be transported in the separate cryostat to a site remote from where it was hyperpolarized prior to reacting the first material with at least one other material to form a mixture including hyperpolarized nuclei. In accordance with a preferred embodiment, the nuclei in the first material includes at least one material selected from the group consisting of $^{13}$C, $^{15}$N, $^1$H, $^{33}$P and $^{29}$Si.

In further accordance with the disclosure, the method may further include substantially increasing the temperature of the first material without melting or sublimating the material after the initial temperature increase that results in nuclei in the first material becoming hyperpolarized. For example, the temperature may be increased from a first temperature substantially below the temperature at which the $T_1$ of the first material experiences a minimum to a second temperature substantially above the temperature at which the $T_1$ of the first material experiences a minimum. In accordance with one embodiment, the temperature of the first material is increased from a temperature below about 10K to a temperature of about 200K. In accordance with another embodiment, the temperature of the first material may be increased in the presence of a magnetic field at a rate wherein less than about 90 percent of polarization imparted to nuclei in the first material is lost. In accordance with certain preferred embodiments, the temperature of the first material may be increased in the presence of a magnetic field at a rate wherein less than about 80, 70, 60, 50, 40, 30, 20, 10 or 5 percent of polarization imparted to nuclei in the first material is lost. If desired, the first material may be transported to a location within the fringe field of an MR system after the first material has reached the second temperature.

In further accordance with the disclosure, the method may additionally include the step of removing the first material from the polarizing cryostat after the initial temperature increase that results in nuclei in the first material becoming hyperpolarized. By way of further example, the method may further include transferring the first material into a transport cryostat after the initial temperature increase that results in nuclei in the first material becoming hyperpolarized. Accordingly, the transport cryostat may be transported to an end user. The first material may then be transferred from the transport cryostat into a transfer vessel. The transfer vessel may include a permanent magnet or electromagnet for maintaining the first material in a magnetic field. The method may further include increasing the temperature from a first temperature below the temperature at which the $T_1$ of the first material experiences a minimum to a second temperature above the temperature at which the $T_1$ of the first material experiences a minimum. The temperature may be raised to the second temperature at substantially the same time the first material is transferred into the transfer vessel. The temperature may be raised to the second temperature in less than about thirty seconds in a magnetic field having a strength between about 0.1 Tesla and about 10 Tesla.

In further accordance with the disclosed embodiments, the method may further include the step of disposing the first material in a mixing device within the fringe field of a MR system. Preferably, at least a portion of the reacting step occurs within the mixing device. If a transfer vessel is used, the magnet of the transfer vessel is preferably turned off or otherwise deactivated or shielded prior to performing an MR system operation.

In further accordance with the disclosure, the first material may include an acid and the at least one other material may include a base. On the other hand, the first material may include a base and the at least one other material may include an acid. Accordingly, the acid may include an acid selected from the group consisting of acetic acid, formic, lactic and pyruvic acid. Preferably, the acid is isotopically enhanced in one or more of its carbon sites with $^{13}$C. In accordance with one embodiment, the at least one other material includes sodium, such as in the form of sodium hydroxide and/or sodium bicarbonate. In accordance with still a further aspect, the first material may be a liquid, solid, and/or gas at standard temperature and pressure ("STP"). In accordance with one embodiment, the first material may be frozen in a high surface area configuration such that it has a surface area to volume ratio greater than about 0.1 m$^2$/g.

In further accordance with the present disclosure, a method of magnetic resonance (MR) investigation of a subject including a human subject or other organism is provided. The method includes producing a mixture including hyperpolarized nuclei as described herein, administering the mixture to the subject, exposing the subject to radiation of a frequency selected to excite nuclear spin transitions in the hyperpolarized nuclei, and detecting magnetic resonance signals from the subject.

In further accordance with the disclosure, the method may further include generating at least one of an image, dynamic flow data, diffusion data, perfusion data, physiological data or metabolic data from the detected signals. The hyperpolarized nuclei in the mixture preferably have a $T_1$ value of at least 5 seconds at a field strength in the range 0.01-5 T and at a temperature in the range of 20-40° C.

The disclosure further provides a method of producing a material including hyperpolarized nuclei. The method includes increasing the state of polarization of a first material in the absence of a source of free electrons (e.g., TA, discussed above) or paramagnetic impurities (e.g., EPA, discussed above) at a temperature below about 10K in the presence of a magnetic field, increasing the temperature of the first material without melting it resulting in nuclei in the first material becoming hyperpolarized, and reacting the first material with at least one other material to form a mixture including hyperpolarized nuclei. The mixture may include a solution, among other types of mixtures.

In further accordance with the disclosure, the methods described herein may include embodiments wherein the first material includes a methyl group. By way of further example, the methods described herein may include embodiments wherein the resulting mixture includes pairs of bonded nuclei. Preferably, at least a portion of the bonded nuclei are hyperpolarized.

The disclosure further provides a method of producing a material containing hyperpolarized nuclei. The method includes formatting a first material including a methyl group into a high surface area configuration, increasing the nuclear polarization of the first material, and increasing the temperature of the first material from a first temperature below the temperature at which the $T_1$ of the first material experiences a minimum to a second temperature above the temperature at which the $T_1$ of the first material experiences a minimum without melting or sublimating the first material within a time period less than about thirty seconds. The disclosure also provides a method of producing a material containing hyperpolarized nuclei. The method includes formatting a first material including a methyl group into a high surface area configuration, increasing the nuclear polarization of the first material, and increasing the temperature of the first material from a first temperature below the temperature at which the $T_1$ of the first material experiences a minimum to a second temperature above the temperature at which the $T_1$ of the first material experiences a minimum without melting or sublimating the first material within a time period less than about thirty seconds, wherein less than about 90 percent of the polarization is lost when increasing the temperature. In further accordance with the disclosure, the first material may be reacted with at least one other material to form a mixture including hyperpolarized nuclei. In accordance with certain preferred embodiments, less than about 80, 70, 60, 50, 40, 30, 20, 10 or 5 percent of the polarization is lost when increasing the temperature.

The disclosure yet further provides a method of producing a material containing hyperpolarized nuclei. The method includes hyperpolarizing a first material, and increasing the temperature of the first material from a first temperature below the temperature at which the $T_1$ of the first material experiences a minimum to a second temperature above the temperature at which the $T_1$ of the first material experiences a minimum without melting or sublimating the first material.

The disclosure still further provides a method of producing a material containing hyperpolarized nuclei. The method includes formatting a first material into a high surface area configuration and, in a polarizing cryostat, exposing the first material to $^3$He at a temperature below about 10K and a magnetic field in a manner sufficient to substantially increase the polarization of the first material. The method also includes reacting the first material with at least one other material to form a mixture including hyperpolarized nuclei.

The disclosure also provides a method of producing a mixture including hyperpolarized nuclei including providing a precursor including hyperpolarized nuclei, disposing the precursor in the stray field of an MR system, and reacting the precursor with at least one other material to form a mixture including hyperpolarized nuclei.

In further accordance with the disclosure, an embodiment of a system for producing a material containing hyperpolarized nuclei is provided. The system includes a polarizing cryostat having a vessel for exposing a first material formatted into a high surface area configuration to $^3$He at a temperature below about 10K and a magnet adapted and configured to provide a magnetic field in a manner sufficient to substantially increase the polarization of the first material. The system further includes a first heat source for increasing the temperature of the first material without melting or sublimating the first material resulting in nuclei in the first material becoming hyperpolarized. The system still further provides a mixing device for reacting the first material with at least one other material to form a mixture including hyperpolarized nuclei.

In further accordance with the disclosure, the mixture may be a solution. The system may further include a second heat source for melting the first material to permit the first material to react. The second heat source may include the material with which the first material is mixed in the mixing device. For example, the first material may be melted by dropping it into the material with which the first material is mixed. By way of further example, the first material may melt prior to contacting the material with which the first material is mixed. The system may further include means for exposing the first material to $^4$He after exposing the first material to $^3$He.

In accordance with a further aspect, the system may further include a transport cryostat in which the first material in a hyperpolarized condition is stored. The transport cryostat is preferably suitable for transporting the first material to a site remote from where the first material was hyperpolarized. In accordance with a preferred embodiment, the nuclei in the first material includes at least one material selected from the group consisting of $^{13}$C, $^{15}$N, $^1$H, $^{31}$P and $^{29}$Si.

In accordance with another aspect, the system may include means for substantially increasing the temperature of the first material without melting or sublimating the material after the first material becomes hyperpolarized. The system may be adapted and configured to increase the temperature from a first temperature substantially below the temperature at which the $T_1$ of the first material experiences a minimum to a second temperature substantially above the temperature at which the $T_1$ of the first material experiences a minimum. The system is preferably adapted and configured to increase the temperature of the first material from a temperature below about 10K to a temperature of about 200K.

In further accordance with the present disclosure, the system may include a transfer vessel for receiving the first material from the transport cryostat. The transfer vessel preferably includes a magnet for maintaining the first material in a magnetic field. In accordance with a further embodiment, the system includes a mixing device for receiving the first material from the transfer vessel. The mixing device and transfer vessel are preferably adapted and configured to be operated within the fringe field of a MR system. The magnet of the transfer vessel can be adapted and configured to be turned off prior to performing an MR system operation.

In further accordance with the system, the first material can be a liquid, solid, and/or a gas at STP. The first material is preferably in a high surface area configuration that has a surface area to volume ratio greater than about 0.1 m$^2$/g.

The disclosure provides a system of magnetic resonance (MR) investigation of a subject including a human subject or other organism. The MR system includes means for producing a mixture including hyperpolarized nuclei as described herein and an injector for administering the mixture to the subject. The system further includes at least one radio frequency coil for exposing the subject to radiation of a frequency selected to excite nuclear spin transitions in the hyperpolarized nuclei, and a detector for detecting magnetic resonance signals from the subject.

In further accordance with the disclosure, the system may further include means for generating at least one of an image, dynamic flow data, diffusion data, perfusion data, physiological data or metabolic data from signals received from the detector.

The disclosure also provides an exemplary system for producing a material including hyperpolarized nuclei. The system includes means for increasing the state of polarization of a first material in the absence of a source of free electrons or paramagnetic impurities at a temperature below about 10K in the presence of a magnetic field. The system further includes means for increasing the temperature of the first material without melting it resulting in nuclei in the first material becoming hyperpolarized. The system also includes means for reacting the first material with at least one other material to form a mixture including hyperpolarized nuclei.

In further accordance with the disclosure, the disclosed systems may utilize a first material that includes a methyl group. If desired, the disclosed systems may be used to make a mixture that includes pairs of bonded nuclei. Preferably, at least a portion of the bonded nuclei are hyperpolarized.

In further accordance with the disclosed embodiments, a system for producing a material containing hyperpolarized nuclei is provided. The system includes means for formatting a first material including a methyl group into a high surface area configuration and means for increasing the nuclear polarization of the first material. The system further includes means for increasing the temperature of the first material from a first temperature below the temperature at which the $T_1$ of the first material experiences a minimum to a second temperature above the temperature at which the $T_1$ of the first material experiences a minimum without melting or sublimating the first material within a time period less than about thirty seconds.

In further accordance with the disclosure, a system for producing a material containing hyperpolarized nuclei is provided. The system includes means for formatting a first material including a methyl group into a high surface area configuration, and means for increasing the nuclear polarization of the first material. The system further includes means for increasing the temperature of the first material from a first temperature below the temperature at which the $T_1$ of the first material experiences a minimum to a second temperature above the temperature at which the $T_1$ of the first material experiences a minimum without melting or sublimating the first material within a time period less than about thirty seconds, wherein less than about 90 percent of the polarization is lost during the warming step. In accordance with certain preferred embodiments, less than about 80, 70, 60, 50, 40, 30, 20, 10 or 5 percent of the polarization is lost during the warming step.

In further accordance with the disclosure, the system may include means for reacting the first material with at least one other material to form a mixture including hyperpolarized nuclei.

In yet further accordance with the disclosure, a system for producing a material containing hyperpolarized nuclei is provided. The system includes means for hyperpolarizing a first material and means for increasing the temperature of the first material from a first temperature below the temperature at which the $T_1$ of the first material experiences a minimum to a second temperature above the temperature at which the $T_1$ of the first material experiences a minimum without melting or sublimating the first material.

In still further accordance with the disclosure, system for producing a material containing hyperpolarized nuclei is provided. The system includes means for formatting a first material into a high surface area configuration, a polarizing cryostat having means for exposing the first material to $^3$He at a temperature below about 10K, and a magnet for generating a magnetic field in a manner sufficient to substantially increase the polarization of the first material. The system also includes a mixing device for reacting the first material with at least one other material to form a mixture including hyperpolarized nuclei.

In further accordance with the disclosed embodiments, a system for producing a mixture including hyperpolarized nuclei is provided. The system includes means for providing a precursor including hyperpolarized nuclei and means for disposing the precursor in the stray field of an MR system. The system further includes means for reacting the precursor with at least one other material to form a mixture including hyperpolarized nuclei.

In accordance with another embodiment, the disclosure provides further embodiments of manufacturing hyperpolarized material. One such exemplary method includes providing a first material to be polarized, increasing the polarization of at least one nuclei contained in the first material, and transferring the increased polarization of the at least one nuclei to other nuclei in the first material.

In accordance with further aspects, the first material preferably includes a methyl rotor group, the polarization of at least one hydrogen nuclei in the methyl rotor group is increased in the polarization step, and the increased polarization of the at least one hydrogen nuclei is transferred to other nuclei in the first material in the transferring step. The first material is preferably substantially purged of paramagnetic agents and polarization agents prior to polarization. For example, the first material is preferably substantially purged of TA and EPA prior to polarization. The first material is preferably isotopically enhanced by substituting one or more of its atomic sites with at least one of $^{129}$Xe, $^{13}$C, $^{15}$N, $^1$H, $^2$H, $^{31}$P, $^{19}$F and $^{29}$Si.

In accordance with another aspect, the polarization step preferably includes exposing the first material to a polarizing environment. This preferably includes at least one of (i) decreasing the temperature of the first material, and (ii) subjecting the first material to an increased magnetic field, wherein the first material is exposed to the polarizing environment for a time sufficient to polarize at least one hydrogen nuclei contained in the first material to thermodynamic equilibrium. The first material may be a solid, liquid and/or gas at STP. Preferably, the method further includes the step of extracting the first material from the polarizing environment (e.g., crysostat) while the first material is in the solid state. Also, the polarization time is preferably sufficient to polarize the at least one hydrogen nuclei in the methyl group.

In accordance with another preferred aspect, the method can further include directing the first material from the polarizing environment through a region of decreased magnetic field to a second location to facilitate the transfer of polarization from the at least one nuclei to other nuclei in the first material after the polarization step. Preferably, the first material is transferred from the polarizing environment through the region of decreased magnetic field to the second location over a time period greater than $T_2$ but less than $T_1$. For example, the first material can be transferred from the polarizing environment to the second location in less than 1.0 seconds, than 0.1 seconds, less than 0.01 seconds, or in about 0.001 seconds, if desired.

In accordance with still further aspects, the second location can include a cryogenic environment with a magnetic field. For example, the second location can include a transport cryostat including a magnet, wherein the magnet applies a magnetic field to the first material at a low temperature. Preferably, the first material is in a solid state after the polarization step and the first material is directed to the second location by accelerating it with fluid pressure. The first material can be directed to the second location by directing it through a conduit with a compressed gas. For example, the first material can be directed through the conduit by the compressed gas at a speed in excess of 10 m/s, 100 m/s or 1000 m/s. The compressed gas preferably includes helium, and may include $^3$He.

In accordance with yet further aspects, the second location can include a melting vessel for melting the first material. In one embodiment, the region of decreased magnetic field can include magnetic shielding to lower the strength of the magnetic field in the region of decreased magnetic field to a magnitude less than the Earth's background field. If desired, the method can further include warming the first material while in the polarizing environment prior to expulsion. The warming step preferably increases the temperature of the first material from below the temperature at which the $T_1$ of the first material experiences a minimum ($T_{min}$) to a second temperature above the temperature at which the $T_1$ of the first material experiences a minimum ($T_{min}$) without substantially melting or sublimating the first material.

In accordance with a further embodiment, the disclosure provides a method for manufacturing a hyperpolarized material that includes providing a first material to be polarized in the form of a high surface area powder, increasing the polarization of at least one nuclei contained in the first material within a vessel in a polarizing environment by performing at least one of: (i) decreasing the temperature of the first material, and (ii) subjecting the first material to an increased magnetic field. The first material is exposed to the polarizing environment for a time sufficient to polarize at least one nuclei contained in the first material to thermodynamic equilibrium. The method further includes the step of transferring the increased polarization of the at least one nuclei to other nuclei in the first material while directing the first material from the polarizing environment through a region of decreased magnetic field to a second location.

In accordance with further aspects, the high surface area first material can be exposed to $^3$He for a time sufficient to polarize at least one nuclei contained in the material. Subsequent to $^3$He exposure, the high surface area formatted first material can be exposed to $^4$He to remove the $^3$He. Subsequent to exposure to $^4$He, the first material can be warmed without substantially melting or sublimating the first material, resulting in nuclei in the material becoming hyperpolarized. Warming preferably increases the temperature of the first material from below the temperature at which the $T_1$ of the first material experiences a minimum ($T_{min}$) to a second temperature above the temperature at which the $T_1$ of the first material experiences a minimum ($T_{min}$) without substantially melting or sublimating the first material. The first material can be maintained in a magnetic field during the warming step. The first material is preferably directed from the polarizing environment to a second location in a time greater than $T_2$ and less than $T_1$. The second location preferably includes a cryogenic environment with a magnetic field. For example, the second location can include a transport cryostat including a magnet, wherein the magnet applies a magnetic field to the first material at a low temperature.

In accordance with a further aspect of the method, the first material can be polarized using a technique selected from the group consisting of (i) dynamic nuclear polarization, (ii) the Nuclear Overhauser effect, (ii) parahydrogen induced polarization, (iii) exposing the nuclei of the first material to hyperpolarized nuclei of a previously hyperpolarized gas, (iv) exposing the first material to a brute force environment and combinations thereof.

The disclosure further provides a method of forming a hyperpolarized solution, comprising hyperpolarizing a first material that is a liquid at STP in as set forth above, and mixing the first hyperpolarized material with a second material to form a solution. The first material can be reacted with the second material to form the solution. The first material can include an acid and the second material includes a base, or vice versa. The acid can include one or more of acetic acid, lactic acid, pyruvic acid and formic acid. In one embodiment, the acid(s) can be isotopically enhanced at one or more of its atomic sites by substitution of one or more isotopes selected from the group consisting of $^{13}$C, $^{15}$N, $^1$H, $^2$H, $^{31}$P, $^{19}$F and $^{29}$Si. In accordance with a further aspect, the second material can include sodium, such as in the form of sodium hydroxide and/or sodium bicarbonate.

In accordance with further aspects, the first material can be a solution at STP, and the method can further include mixing the first material with a second material to form a second solution. In another embodiment, a method is provided as set forth above wherein the first material is a solid at STP, and the method further includes mixing the first material with a second material to form a solution. In still another embodiment, the method can further include mixing the first material with a second material to form a suspension. In one embodiment, the first material is a solid at STP, and the method can further include mixing the first material with a second material to form a colloid. In another embodiment, the first material can be a solid at STP, and the method can further include mixing the first material with a second material to form an emulsion. In yet another embodiment, the first material can be a solid at STP, and the method can further include mixing the first material with a second material to form a composite material. In another embodiment, the method can include encapsulating the first material in an encapsulating medium. The encapsulating medium can be porous.

In accordance with another aspect, the method can further include storing the first material in a hyperpolarized condition in the transport cryostat, and transporting the first material in the transport cryostat to a site remote from where it was hyperpolarized. If desired, the first material can be transported to a location within the fringe field of an MR system. The method can then include increasing the temperature of the first material from a first temperature below $T_{min}$ to a second temperature above $T_{min}$. The first material can then be disposed in a mixing device within the fringe field of the MR system. The first material can then react (e.g., chemically) with a second material within the mixing device. Preferably, the magnet of the transfer vessel is turned off prior to performing an MR system operation. The above steps can be carried out regardless of the initial mechanism used to hyperpolarize the first material. In accordance with still another embodiment, the first material is partially or fully deuterated.

In accordance with another embodiment, a method is provided as set forth above, but further comprising increasing the temperature of the first material from a first temperature below $T_{min}$ to a second temperature above $T_{min}$ while the first material is situated in the transport cryostat or being directed into a transfer vessel. If desired, the first material can then be directed into the transfer vessel, wherein the transfer vessel is adapted and configured to maintain the first material at an elevated magnetic field and at a temperature lower than the melting point of the first material. For example, the transfer vessel can include a magnet and the temperature of the first material can be maintained in the transfer vessel at least in part with the aid of dry ice. In accordance with a further aspect, the method can further include mixing the first material with a second material to form a mixture. The mixing step can include melting the first material in the presence of an elevated magnetic field. The mixing step can occur while the first material is directed into the transfer vessel, while the first material is situated in the transfer vessel or in a further vessel in the fringe field of the MR system. The first material can react with a second material within the transfer vessel.

The disclosure also provides a system for manufacturing a hyperpolarized material. The system includes means for delivering a first material to be polarized to a polarizing region, means for increasing the polarization of at least one nuclei contained in the first material while in the polarization region, and means for transferring the increased polarization of the at least one nuclei to other nuclei in the first material. If desired, the first material can include a methyl rotor group, and the polarization of at least one hydrogen nuclei in the methyl rotor group can be increased by the means for increasing the polarization, and the increased polarization of the at least one hydrogen nuclei can be transferred to other nuclei in the first material by the transferring means. The first material is preferably substantially purged of paramagnetic agents and polarization agents prior to polarization.

In accordance with a further aspect of the system, the means for transferring can include means for directing the first material from the polarizing region through a region of decreased magnetic field to a second location to facilitate the transfer of polarization from the at least one nuclei to other nuclei in the first material. The means for directing can be adapted and configured to transfer the first material from the polarizing environment through the region of decreased magnetic field to the second location over a time period greater than $T_2$ but less than $T_1$. The means for directing is preferably adapted and configured to transfer the first material from the polarizing environment through the region of decreased magnetic field to the second location, for example, in less than 1.0 seconds, less than 0.1 seconds, less than 0.01 seconds or in about 0.001 seconds, if desired.

In accordance with yet a further aspect, the second location can include a cryogenic environment with a magnetic field. For example, the second location can include a transport cryostat including a magnet, wherein the magnet applies a magnetic field to the first material at a low temperature. Preferably, the first material is in a solid state after polarization and the first material is directed to the second location by accelerating it with fluid pressure. In one embodiment, the first material is directed to the second location by directing it through a conduit with a compressed gas at a speed in excess of 10 m/s, in excess of 100 m/s, in excess of 1000 m/s, or as desired. The compressed gas can include helium, and may include $^3$He. By way of further example, the second location can include a melting vessel for melting the first material. In one embodiment, the region of decreased magnetic field includes magnetic shielding to lower the strength of the magnetic field in the region of decreased magnetic field to a magnitude less than the Earth's background field. In another aspect, the system can further include means (such as an electrical resistance heater) for warming the first material while in the polarizing environment. The warming means preferably increases the temperature of the first material from below the temperature at which the $T_1$ of the first material experiences a minimum ($T_{min}$) to a second temperature above the temperature at which the $T_1$ of the first material experiences a minimum ($T_{min}$) without substantially melting or sublimating the first material. In accordance with still a further aspect, the first material can be in the form of a high surface area powder prior to polarization. Moreover the nuclei of the first material can be polarized initially using a technique selected from the group consisting of (i) dynamic nuclear polarization, (ii) the Nuclear Overhauser effect, (ii) parahydrogen induced polarization, (iii) exposing the hydrogen nuclei to hyperpolarized nuclei of a previously hyperpolarized gas, (iv) exposing the first material to a brute force environment and combinations thereof.

The disclosure further provides a beneficial agent including a material having at least one methyl group, wherein the carbon nuclei within the methyl group is hyperpolarized and wherein the beneficial agent is adapted and configured to be in a solid state outside of a polarizing cryostat. The beneficial agent can be made according to any of the teachings herein.

The disclosure further provides a method of performing NMR spectroscopy. The method includes introducing a hyperpolarized material made in accordance with any of the teachings herein into a region of interest, transmitting a pulse of electromagnetic energy into the region of interest to excite the hyperpolarized encapsulated material, and receiving NMR spectra from the region of interest. The NMR spectra of an in vitro or in vivo sample can be analyzed. In accordance with a further aspect, another method is provided including hyperpolarizing a material suitable for being metabolized in a biological process in accordance with any of the teachings herein, introducing the hyperpolarized material into a region of interest; and receiving NMR data or MR images indicative of metabolism of the hyperpolarized material.

The accompanying drawings, which are incorporated in and constitute part of this specification, are included to illustrate and provide a further understanding of the disclosed methods and systems. Together with the description, the drawings serve to explain principles of the disclosure.

DETAILED DESCRIPTION OF PREFERRED EMBODIMENTS

Figure 1:
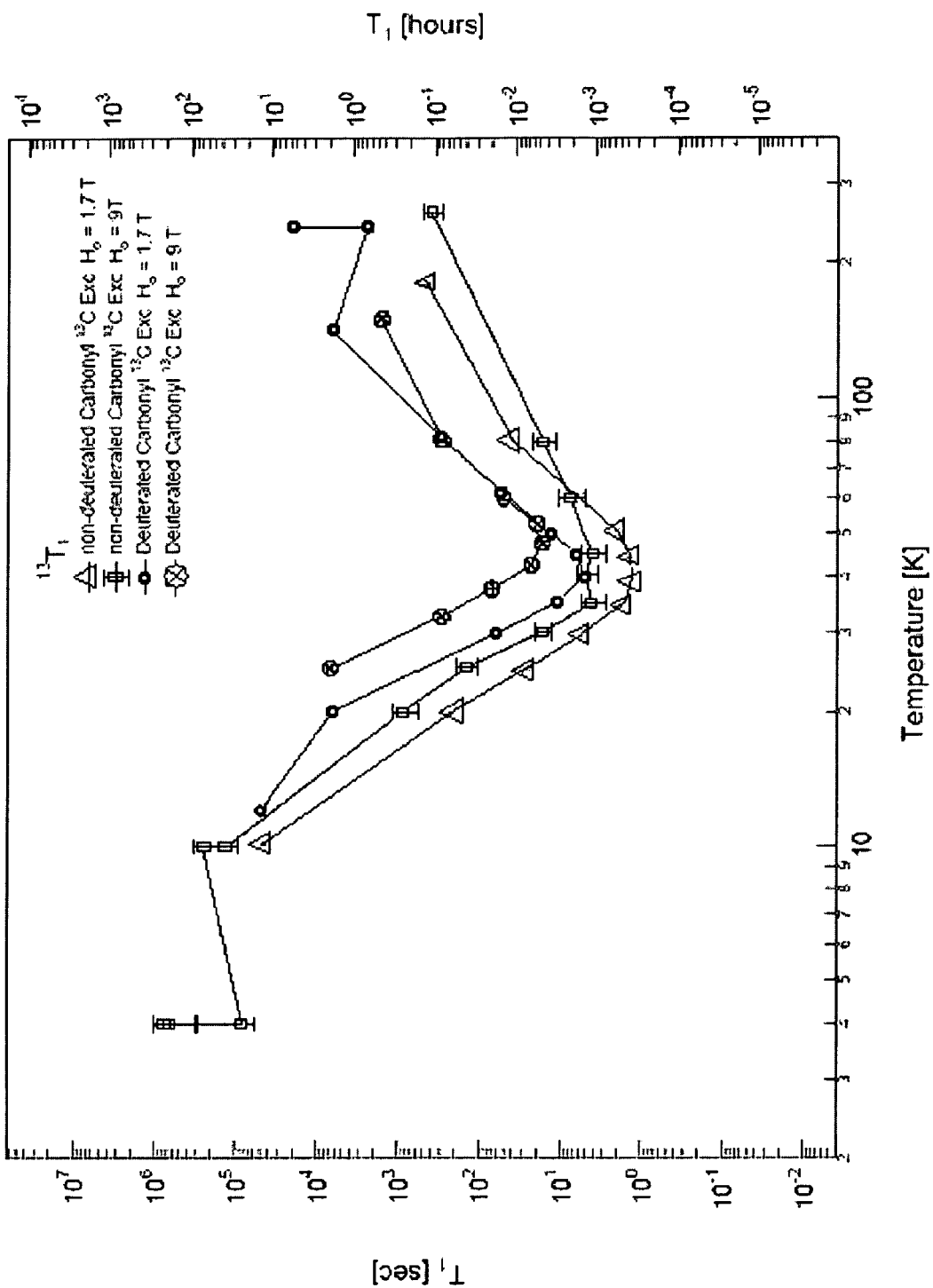
FIG. 1 depicts nuclear polarization decay times ("$T_1$") vs temperature in differing magnetic fields for several different protonated and deuterated samples of frozen 1-$^{13}$C enriched acetic acid.

Reference will now be made in detail to the present preferred embodiments of the disclosed embodiments, examples of which are illustrated in the accompanying drawings. The method and corresponding steps of the disclosed embodiments will be described in conjunction with the detailed description of the system.

It is one object of this disclosure to provide exemplary methods whereby nuclei in various molecules may be hyperpolarized without the need for the addition (or use) of toxic catalysts such as a TA/EPA or other catalysts or any polarizing agents (whether or not toxic). In accordance with a preferred embodiment, nuclei in molecules are hyperpolarized which may then be reacted to form $^{13}$C-bearing molecules of biological interest such as acetates and pyruvates in solution.

In accordance with a particularly preferred embodiment, sodium acetate including hyperpolarized nuclei may be provided. Sodium acetate can play a particularly vital role as a reporter on the metabolic process. Although sodium acetate is typically not a substrate found in significant levels in the blood, it is readily taken up and activated to acetyl-CoA. Acetyl-CoA is oxidized in mitochondria by the TCA cycle to form carbon dioxide ($CO_2$). In the process of acetyl-CoA oxidation, NADH is generated, which drives oxidative phosphorylation, the reduction of oxygen workload is tightly coupled to $O_2$ consumption and to the flux of acetyl-CoA through the TCA cycle. Thus, measurement of TCA cycle flux reports the metabolism required for heart function.

In accordance with one exemplary embodiment, a method for making sodium acetate solution including hyperpolarized nuclei may be produced. This may be accomplished, for example, by reacting acetic acid with sodium bicarbonate to produce sodium acetate, water and carbon dioxide gas, wherein nuclei in at least one of the precursors are hyperpolarized. The reaction thus naturally produces a mixture such as a solution that, when optionally combined with buffers, saline or other chemicals, is amenable for in vivo applications as a tracer and/or as a source of metabolic information. Other acids such as lactic, pyruvic and formic acid may additionally or alternatively be used.

Storage and Transfer of Polarized Materials:

Unlike radioactive tracers, the characteristic nuclear polarization decay times ($T_1$) of materials including hyperpolarized nuclei are a function of their ambient environment. Temperature, magnetic field and the physical state of the material (liquid, solid, gas etc.) all play a role in determining how long the induced nuclear polarization will last before it decays away to thermal equilibrium. Under appropriate conditions $T_1$ can be made to be quite long. Longer decay times open up the possibility of transporting HP materials (i.e., materials including hyperpolarized nuclei) over large distances. Thus, HP materials can then be supplied as a consumable, removing the need for the user to site a polarizer on its premises and reducing the cost burden.

In addition to temperature and field, the physical state and the chemical composition of the material influences its nuclear polarization decay time. Applicant has measured the $T_1$ of acetic acid and sodium acetate over a wide range of temperatures and fields. Applicant has discovered that the $T_1$ of hyperpolarized nuclei in sodium acetate is quite short over a wide range of temperature (e.g., from 4 K to 300 K). This is too short for hyperpolarized sodium acetate to be transported over any reasonable distance in any kind of reasonable magnetic field without severe loss of polarization. However, the $T_1$ of acetic acid (deuterated) can be very long at T<15 K and in a moderate magnetic field (typically B~0.1 T). This discovery permits transporting HP acetic acid (i.e., acetic acid including hyperpolarized nuclei) over large distances and supplying it as a consumable item. Because it is sodium acetate, not acetic acid, which is required for use as an in vivo agent, the acetic acid is converted to sodium acetate just before use.

The DNP method described above does not lend itself well to long term transport or storage of a hyperpolarized material. One reason for this is that the TA/EPA present in the frozen HP material shortens the $T_1$ in the solid state. The TA/EPA cannot be removed without melting the material into its liquid state. However, the $T_1$ of $^{13}C$ in materials in the liquid state are typically on the order of 10-60 seconds. For this reason, long term storage and/or transport of materials hyperpolarized using DNP is not feasible. As a result, DNP polarizers are typically sited very close to the NMR/MRI system that is used to analyze the HP materials they produce.

Placing the polarizer near the NMR/MRI system is problematic for a number of reasons. First, the high cost of these machines imposes a very high cost burden on the end user, both in terms of capital equipment costs and overhead. In addition, the limited payload scalability of a DNP machine means only a small number of scans can be performed per unit time. This in turn limits the diagnostic information that can be obtained using an HP material polarized using DNP techniques. Transport of the final product in its liquid form from the DNP polarizer to the patient also consumes time that is then not available for observation of the desired metabolic process.

It is accordingly another object of this disclosure to describe methods and systems for storing and/or transporting HP materials. In accordance with a preferred embodiment, methods and systems are provided for storing and/or transporting materials that may be used as precursors in a chemical reaction to manufacture a material (e.g., solution) of biological interest including hyperpolarized nuclei. The present disclosure permits transportation over significant distances such that the HP materials may be supplied as a consumable material manufactured at a first location and transported to the end user.

Extraction of HP Materials from a Cryostat

Many molecules of biological interest contain a methyl group. Such molecules include sodium acetate, sodium pyruvate, and others. The presence of the methyl group has a profound effect in the handling of HP materials. As can be seen in FIG. 1, the $T_1$ of acetic acid has a minimum well below its melting point. The position of the minimum is somewhat field dependent. The minimum in $T_1$ is a consequence of the rotation of the three $^1H$ nuclei attached to the methyl carbon. These hydrogen nuclei continue to rotate even at low temperatures causing nearby nuclei to relax under field/temperature conditions which would otherwise have very long $T_1$s.

Because of the minimum, low temperature hyperpolarization methods to date have relied on very rapid warming schemes to preserve the polarization of various materials during extraction from the polarizing environment. Typically, this involves exposing the material to superheated water or methanol in the presence of a magnetic field to get the sample to temperatures well above the minimum in a time<<$T_1$.

This approach requires that the amount of material be kept small, so that it may be warmed rapidly. It also means that the polarizer must be very close to the NMR/MRI system that is used for analysis. This is extremely disadvantageous for many user sites where space is at a premium. In addition, when DNP is used to hyperpolarize materials, the DNP device must be kept a certain minimum distance away from the target device (NMR/MRI system).

As noted above, many metabolic substrates contain methyl groups which impose a minimum in $T_1$ at temperatures between the polarizing temperature and the melting temperature. Applicant has discovered that at temperatures much warmer than the minimum, but still much less than the melting or sublimation temperature of the material, $T_1$ is again long enough that short term storage/transport is feasible. This enables the possibility of placing the polarizer (and/or a transport cryostat containing polarized material) well outside the vicinity of the MR magnet. Properly utilizing this discovery requires that the polarized material's temperature be changed from well below the minimum to well above it in a time much less than the relaxation time $T_1$ at any point during this process, without melting or sublimating the material. Once the material is melted its $T_1$ becomes quite short and it must be used immediately.

Applicant has discovered that, by configuring the material to be hyperpolarized into a form that has a high surface area to volume ratio, such as a powder or sinter, the thermal relaxation time of the material can be made very short. This allows its temperature to be adjusted very quickly. This has the significant advantage of allowing materials to be warmed from the very low temperatures (as an example, T<10 K) required for long term storage/transport to the more moderate temperatures suitable for short term transport (as an example T~200 K) without melting and/or undue loss of polarization that may occur as the result of a short $T_1$ somewhere in the temperature profile of the material in question. In accordance with certain preferred embodiments, the temperature of the hyperpolarized material may be increased in the presence of a magnetic field at a rate wherein less than about 90, 80, 70, 60, 50, 40, 30, 20, 10 or 5 percent of polarization imparted to nuclei in the first material is lost.

The advantage of preparing polarized materials in this manner is that they may then be transported over short distances (for example, from one part of the user site to another) using readily available cryogenic materials (e.g., liquid nitrogen or dry ice) and in relatively low magnetic fields. Another advantage is that the melting time of the material is reduced as the temperature differential between its starting point and melting temperature is decreased.

Configuring materials that are solids at room temperature into high surface area powders is relatively straightforward. For example, well known techniques such as ball milling can be used to reduce the particle size of the solid material to less than a micron if desired. When the material to be powderized is a liquid at room temperature a different approach must be used. Ball milling is not useful for many frozen liquids as the heat of milling melts the particles. Applicant has developed methods to produce high surface area frozen powders of various materials that are liquid under normal standard temperature and pressures and that, either intrinsically or as the result of a chemical reaction, make suitable metabolic substrates for HP MR study purposes. Suitable methods are described, for example, in Applicant's U.S. patent application Ser. No. 12/193,536, filed Aug. 18, 2008. The aforementioned patent application also discloses various other mixtures that may be achieved in accordance with the present disclosure (e.g., colloids, suspensions, and the like).

Quantum Relaxation Switch "QRS" Process

Heretofore the use of a "brute force" environment to produce high levels of nuclear polarization in materials other than gases has been problematic because the relaxation time of most nuclei under such conditions is very long. Applicant has discovered that, by configuring the material to be polarized as a high surface powder and exposing the surfaces of the powder to $^3$He, the magnetic relaxation time can be made much shorter and amenable to industrial levels of production. Applicant has further discovered that removal of the $^3$He from the surface of the material can be accomplished by exposing the material to $^4$He. This greatly increases the $T_1$ of the material thus allowing it to be warmed to room temperature without undue loss of polarization. Once the material has been returned to room temperature, nuclei in the material become "hyperpolarized." As alluded to above, that is to say that the nuclear polarization of some nuclei in the material is well above what it would otherwise be in thermal equilibrium. The material including the "hyperpolarized" nuclei can now be used for a variety of NMR/MRI protocols. Most notably, the material can in and of itself be used as an in vivo MR material or it can be reacted as a precursor with another material to form a third material which is itself useful as an NMR/MRI material.

U.S. Pat. No. 6,651,459 (which is incorporated by reference herein in its entirety) describes a technique of producing hyperpolarized gases (i.e., materials that are gaseous at standard conditions). This can be done by way of the following exemplary steps:

1) Configuring the gas as a high surface area powder or sinter. As an illustrative non-limiting example, this can be done by freezing the material out on the surface of an aerogel or, more advantageously, as a high surface area "snow".

2) Cooling the gas to "brute force" (very low temperature, very high magnetic field) conditions where the equilibrium nuclear polarization is very high.

3) Exposing the frozen gas to overlayers of $^3$He. In addition to providing a path for thermal relaxation, the layers of $^3$He act to efficiently magnetically relax those nuclei in the topmost layers of the frozen gas to thermal equilibrium which, in "brute force" conditions, is highly polarized. In this sense the unique properties of $^3$He are employed as a relaxation agent to hasten the nuclei's relaxation to a state of high polarization.

4) Exposing the frozen gas to overlayers of $^4$He. The layers of $^4$He act to efficiently remove the $^3$He from the surfaces of the frozen gas. This effectively isolates the nuclei and allows them to be warmed back to room temperature without undue loss of polarization.

The above process is known as a "Quantum Relaxation Switch" (QRS) since it describes a technique whereby efficient relaxation of nuclei in a brute force environment can be switched "on" and "off" so as to produce highly polarized nuclei that can be warmed to room temperature to produce HP precursor materials or HP materials for a variety of NMR/MRI applications. It is important to note that the process does not require the addition of any catalysts and that the brute force environment can be made highly sterile.

Applicant has discovered that the QRS process may be extended to operate on a wide range of materials, rather than only materials that are gases at standard conditions. This requires that the material to be hyperpolarized be configured in a high surface area. Applicant has further discovered that a wide range of liquids may be frozen and powderized so that their surface area to volume ratio is very high. In particular, liquids such as acetic acid that upon chemical reaction make solutions of metabolic substrates suitable for injection and in vivo NMR/MRI protocols are preferred.

The various discoveries described above constitute methods and systems that fully enable the configuration of various materials as high surface area frozen powders, polarizing the material without exposing the materials to catalysts, extracting the polarized materials from the low temperature environment so that they become hyperpolarized (HP), and transporting the hyperpolarized materials to an end user site. It will be recognized that the recitation of "hyperpolarized material" herein is intended to refer to material including hyperpolarized nuclei. If desired, the hyperpolarized materials may be reacted with other materials to form a third HP material that is of use for MRI/NMR applications (e.g., in vivo MRI applications). In accordance with a preferred embodiment, materials are used that contain molecules of interest for biological MRI applications. The following Example is based partially on experience and partially on insight.

Example 1

Deuterated acetic acid is frozen into high surface area pellets by introducing them into LN2 in a finely divided form of droplets. The surface area of the pellets is measured by BET to be ~5 m$^2$/g. The pellets are placed in the sample chamber of a dilution refrigerator and cooled to T<100 mK in the presence of a 10 T magnetic field. $^3$He is added to the sample chamber to hasten magnetic relaxation. Once the sample is polarized (a process which can be monitored using NMR), $^4$He is added to the sample chamber to remove the $^3$He from the surface of the sample. The sample is warmed to T~5 K and the helium gases are removed. The pellets are removed from the chamber of the polarizing cryostat while being kept in a temperature T<10 K and in a magnetic field>0.1 Tesla. The pellets are transferred to a transport cryostat where similar field/temperature conditions are maintained. After transport, the temperature of the pellets is quickly raised from T<10 K to T~77 K, for example, by immersing them in liquid nitrogen. The pellets can then be removed from the transport cryostat and brought into the vicinity of the MR system using a small magnetic field and a suitable cryogenic material to maintain the polarization. The pellets may be rapidly melted by dropping them into heated sodium hydroxide solution in the presence of a magnetic field to create a hyperpolarized mixture, such as in the form of a hyperpolarized sodium acetate solution (i.e., a sodium acetate solution including hyperpolarized nuclei).

Figure 2:
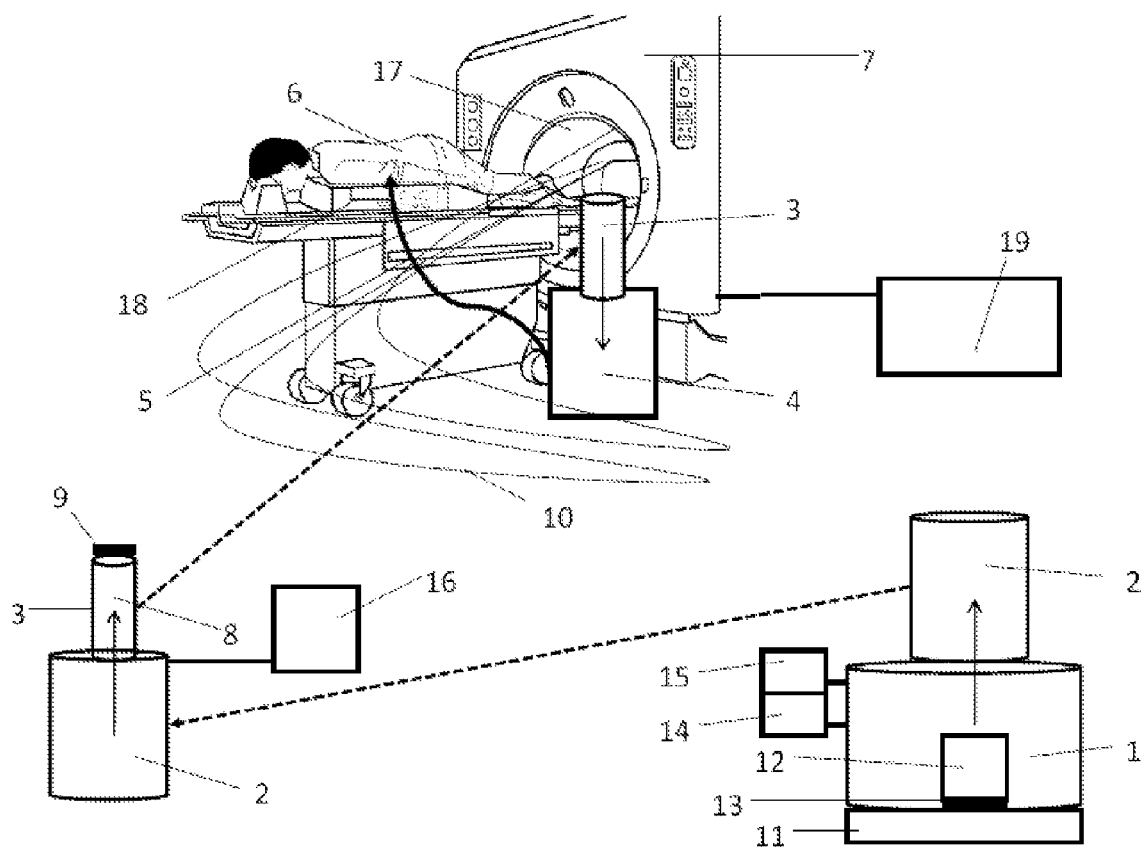
FIG. 2 depicts a schematic view of an exemplary method and system in accordance with the disclosed embodiments.

If desired, the stray field of the MR system can be used to maintain a magnetic field over the hyperpolarized precursor when the precursor is used to make a hyperpolarized mixture. For example, the hyperpolarized precursor (such as an acid or a base including hyperpolarized nuclei) may be transferred from the polarizing cryostat if nearby (or transport cryostat) into a transfer vessel as depicted in FIG. 2. The temperature of the hyperpolarized precursor may then be elevated from a first temperature below the temperature at which the $T_1$ of the first material experiences a minimum to a second temperature above the temperature at which the $T_1$ of the first material experiences a minimum. Preferably, the temperature of the hyperpolarized precursor is elevated from a first temperature substantially below the temperature at which the $T_1$ of the first material experiences a minimum to a second temperature substantially above the temperature at which the $T_1$ of the first material experiences a minimum (e.g., from below about 10K to about 200K). This may be achieved, for example, by immersing the precursor in a liquid cryogen, such as liquid argon, nitrogen, xenon or krypton, that has a boiling point well above the temperature at which the $T_1$ for $^{13}C$ is at a minimum. Alternatively, the precursor can be heated by passing a gas warmed to about 200K over its surfaces.

As illustrated in FIG. 2, material formatted into a high surface area form is polarized in a cryostat 1. Preferably, the material is polarized at a temperature between about 1 mK and 100 mk, more preferably between about 10 mK and about 40 mK. The temperature of the material is then increased, resulting in hyperpolarization (i.e., a state in which the polarization is above that at which it would ordinarily be at thermal equilibrium). The material is then extracted and stored in a transport cryostat 2 that maintains a temperature and magnetic field environment such that decay of the nuclear polarization of the material is slow. This hyperpolarized material may then be transported via the transport cryostat 2 to storage or a terminal location, such as a hospital. The hyperpolarized material is then extracted from the transport cryostat 2 into an interim cryostat or transfer vessel 3 that maintains the hyperpolarized material at a higher temperature and lower magnetic field suitable for short term transport. Before, during or after the transfer of the hyperpolarized material to transfer vessel 3, its temperature is preferably raised as quickly as possible across the temperature at which the $T_1$ for the material is at a minimum.

For example, the temperature increase is preferably performed in a time period less than 30, 20, 10, or most preferably, 5 seconds long. Preferably, the applied field of the transfer vessel 3 is not in excess of 500 Gauss such that it may be brought safely into proximity of the NMR/MRI system. The hyperpolarized material is then ejected from the transfer vessel 3 into a mixing device 4 where it is converted into a mixture, such as a solution, preferably suitable for in vivo injection. The hyperpolarized solution is injected via a sterile line 5 into a patient 6. An NMR/MRI system 7 is then used to carry out a variety of NMR/MRI protocols.

The transfer vessel 3 includes a compartment 8 for receiving the hyperpolarized precursor material, and includes a magnet 9 such as an electromagnet or permanent magnet for maintaining a magnetic field over the material during the transfer process. Preferably, the mixing device 4 and transfer vessel 3 are disposed within the stray magnetic field 10 of the MR system 7. It will be noted that the depicted field lines are merely intended to be illustrative. Advantageously, this permits the hyperpolarized material to be melted in close proximity to the MR system, thus saving time delivering the resultant solution to the subject during which the polarization of will decay. As further illustrated in FIG. 2, the polarizing cryostat 1 includes a magnet 11 for applying a field thereto, a vessel for containing the material to be hyperpolarized, and a heat source for raising the temperature of the material to facilitate hyperpolarization. Also illustrated is the fact that the polarizing cryostat 1 is in operable communication with a source 14 of $^3He$ and a source 15 of $^4He$. A second heat source 16, that is, a source of material that can be used to heat the hyperpolarized material from a temperature below the temperature at which the hyperpolarized material experiences a minimum $T_1$ to a higher temperature is also illustrated. FIG. 2 also illustrates that system 7 includes a transmit RF coil 17, a detector 18 (such as a receive coil array and supporting hardware), as well as a computer terminal/processor 19 for receiving and processing received data.

In a preferred embodiment, magnet 9 is an electromagnet. This permits the magnetic field of the transfer vessel 3 to be selectively deactivated to prevent the field of the transfer vessel 3 from interfering with MR system operation. Alternatively, the field can be well-shielded to minimize interference. If desired, the hyperpolarized precursor for making the hyperpolarized mixture may be made on site in relatively close proximity to the MR system.

Alternative to Relaxation Agents

An alternative to an external relaxation or polarization agent such as those described above is to directly polarize a material containing nuclei that have intrinsically rapid relaxation rates in high B/T conditions. Such nuclei are unusual because under these conditions, as noted above, $T_1$ is typically very long at very low temperatures and can be on the order of weeks to months for temperatures below 100 mK. However, by identifying one or more classes of rapidly relaxing nuclei, it becomes possible to produce high polarizations at high B/T conditions in reasonably short periods of time without the need for an adulterating catalyst or external agent of any kind.

Rapid proton nuclear relaxation rates in molecules containing methyl rotor groups such as potassium acetate have been observed down to 10 K. It is believed that the unusually fast relaxation rate in the hydrogen nuclei is a consequence of quantum tunneling between rotational states in the $CH_3$ group and has been observed in many molecules containing $CH_3$ groups. The tunneling arises because the methyl protons are relatively free to rotate about their symmetry axes. Hindering potentials to rotation arise due to inter and intra molecular interactions between the methyl protons and their environment. Thus, a methyl rotor can be well described as a 3 dimensional quantized harmonic oscillator with a hindering potential that depends on the details of the molecular environment and the crystal structure in the solid state.

When the hindering potential(s) separating the methyl protons are very high the proton rotor is localized in a fixed location. There are three degenerate positions for the rotor. When the hindering potential(s) are lower, quantum tunneling between these positions becomes possible. This splits the degeneracy so that there is a single ground state (typically labeled A) and two excited states (typically labeled $E_a$ and $E_b$), which correspond to clockwise or counterclockwise rotation. At sufficiently low temperatures (typically, T<10 K), where the methyl rotors are in their ground state, quantum tunneling between the A and E states goes on at a fixed frequency labeled $\omega_{0T}$.

Quantum tunneling in solid $^3$He layers has been observed to be a temperature independent effect that persists down to arbitrarily low temperatures and leads to relatively rapid relaxation rates in solid $^3$He; the presence of quantum tunneling in $^3$He is the basis for the method described in U.S. Pat. No. 6,651,459. Similarly, quantum tunneling between rotational states in $CH_3$ groups reduces the relaxation rate of the methyl protons, which would otherwise be expected to become extremely long as T→0. In the limit of low temperatures the $T_1$ relaxation time of the methyl protons is governed by the following equation:

$$T_1^{-1} = C_{BB} \sum_{n=1}^{2} \frac{n^2 \tau_c^2}{1 + \omega_{0T}^2 \tau_o^2}$$

where $\tau_c$=correlation time and $C_{EE}$=constant. This equation shows that in the low temperature limit $T_1$ is a constant since $\omega_{0T}$ does not depend on the ambient magnetic field or temperature.

Thus, at sufficiently low temperatures and for magnetic fields where $\omega_{0T} > \omega_L$ ($\omega_L$=Larmor frequency=42.6 MHz/Tesla for protons) the $T_1$ of the protons in a methyl rotor is both temperature and field independent. This is very different from $T_1$ for molecules that do not exhibit quantum tunneling where $T_1$ is expected to increase exponentially with decreasing temperature in this range. A surprising consequence of this is that saturation polarization of protons in $CH_3$ groups can be rapidly produced even under very high B/T conditions. This occurs as a result of the temperature independent quantum tunneling of protons in the $CH_3$ group and without the addition of a polarizing agent such as a trityl radical or an externally added relaxation agent.

Many molecules of interest for in vivo MR contain a methyl group. These include acetate and pyruvate, for example, among others. In other molecules a methyl group may be incorporated through chemical processes well understood in the art so that at least one or more methyl groups can be attached to the molecule.

One aspect of the present disclosure relates to a method of rapidly producing saturated polarization of one set of nuclei in a molecule, such as the protons in a $CH_3$ group. Polarizing nuclei directly on the molecule of interest has many advantages over the use of an external relaxation agent or polarizing agent. First, as noted above, many relaxation agents and polarizing agents are toxic. Material handling becomes much easier as there is no concern about proper dispersion of an external agent. Nor is there a need to configure the material in a high surface area format as there is to use $^3$He as an effective relaxation agent.

The methyl protons themselves are of little interest for in vivo MR, because their relaxation rate in solution at room temperature is generally too fast. What is of greater interest are the nearby methyl and carbonyl carbons. These tend to have longer $T_1$s (the carbonyl in particular). Moreover, the chemical shift of carbons is much wider than for protons, making them easier to resolve in a spectroscopy study. For this reason, a further aspect of the present disclosure relates to methods for efficiently transferring polarization between nuclei in a molecule; in particular, from methyl protons to nearby methyl and/or carbonyl carbons so that they be utilized in an MR study.

Several methods exist in the art to transfer polarization between nuclei in a molecule. For example, pulse sequences can be used to transfer polarization between nuclei. However, these are not suitable for scalable production of hyperpolarized materials as they require highly homogenous magnets and an NMR resonator that can typically only handle a small amount of material at a time. An easier and more scalable method is to expose the material to a low field. Polarization may be transferred between nuclei in a molecule by exposing it to a low magnetic field. This is known as low field thermal mixing ("LFTM"). In this process, the molecule is exposed to a magnetic field sufficiently low such that the local dipolar field of a given nuclei upon another nearby nuclei exceeds that of the ambient field. Under these circumstances the "spin temperature" of the two nuclei will equilibrate at a rate equal to:

$$\frac{1}{\tau} = \frac{1}{T_2} \exp\frac{(\gamma_1 - \gamma_2)^2 B^2}{(\gamma_1 + \gamma_2)^2 B_L^2}$$

Where B is the ambient magnetic field, $B_L$ is the local dipolar field of nuclei 1 on nuclei 2, and $\gamma_{1,2}$ is the gyromagnetic ratio of nuclei 1,2 respectively. $B_L$ is typically on the order of 1-5 G for neighboring nuclei in a molecule so B must be on this order as well for rapid transfer of polarization. It is readily seen that for $B<B_L$, $\tau \to T_2$. $T_2$ in the solid state is typically on the order of tens of microseconds so polarization exchange takes place very quickly for $B<B_L$.

LFTM has been used to produce polarized materials in the solid state. For example, in U.S. Pat. No. 6,466,814, a sample of solid 2-$1^{3C}$-2,2-bis(trideuteromethyl)-1,1,3,3-tetradeuteropropane-1,3-diol was polarized to $^{13}$C thermodynamic equilibrium at 6.65 T and 2.5 K by repeatedly pulling it in and out of the polarizing magnet and into the stray field of ~70 G for ~1 second. These examples and others demonstrate that it is possible to transfer polarization from protons to heteronuclei such as $^{13}$C using low field thermal mixing.

However exposure of materials to low fields can also lead to rapid depolarization because $T_1$ in the solid state is typically a strong function of the ambient field. For example, in U.S. Pat. No. 6,466,814, solid 2-$^{13}$C-2,2-bis(trideuteromethyl)-1,1,3,3-tetradeuteropropane-1,3-diol was polarized using LFTM, extracted by pulling it out of the polarizing cryostat at the end of a sample stick and finally dissolved to form a solution. The resultant enhancement factor vis-à-vis $^{13}$C was measured in solution to be ~12. The total potential gain, or enhancement factor, was ~>100 so more than 90% of the polarization induced at high B/T was lost during extraction.

Conventionally, the "enhancement factor" is considered to be the ratio of the hyperpolarized NMR signal intensity (itself defined as the integral of the Fourier Transform line) divided by the NMR signal intensity of the molecule at thermal equilibrium. To measure this quantity in practice, it is typical to collect a series of Free Induction Delay ("FID") signals with an rf tuning set during a series of NMR pulses immediately after the hyperpolarized sample is inside the NMR magnet. This test is then repeated after the sample reaches thermal equilibrium, which for all practical purposes is on the order of ~5 $T_1$, or about 4-5 minutes for acetic acid, for example. The ratio of the two FID signals is the enhancement factor. It will be understood that the enhancement factor will naturally be affected by how quickly the sample can be measured initially. An enhancement factor of 12, such as described above, means that the signal intensity from the hyperpolarized solution was 12 times what it would have been for the same solution in the same spectrometer had the sample not been enhanced.

For the reasons discussed above, most hyperpolarization schemes have relied on dissolving the polarized material directly in the polarizing cryostat so that the material is never exposed to a low field. Once in the liquid state, external agents can be quickly removed and also $T_1$ of the HP material is less sensitive to external relaxants and/or field changes. U.S. Pat. No. 7,102,354 describes a method of doing this where the material is dissolved by injection of hot water.

However, as noted above, a negative consequence of this is that hyperpolarized materials cannot be stored for long periods of time or transported over significant distances; with the exception of noble gasses this can only be realized if the material can be kept in the solid state. Thus there is a need in the art for a method of extracting polarized materials in the solid state from a polarizing cryostat without undue loss of polarization. The present disclosure describes how to accomplish this objective below.

In accordance with one embodiment, for in vivo MR applications, the hyperpolarized material is rendered in a form in which it can be introduced in vivo. Depending on the application and material this can take the form of a solution, suspension, colloid or other type of mixture. A suspension could furthermore include solid pellets suspended in a physiologically tolerable liquid or an encapsulation of a solid or liquid hyperpolarized material.

U.S. Pat. No. 6,466,814 and U.S. Pat. No. 6,278,893 describe the manufacture of HP solutions by dissolving a hyperpolarized solid in a physiologically tolerable liquid. But they do not teach the use of a liquid and/or a predissolved solution. For many applications it would be superior if the hyperpolarized material were a liquid at STP or a predissolved solution. One reason for this is that liquids can be directly pelletized, for example by droppering them into a cryogenic liquid such as liquid nitrogen. Pelletizing a solid, in particular a solid that is a powder, may require that it be mixed with binders or other additives that will reduce the overall payload of hyperpolarizable material in the pellet. Furthermore, liquids melt and mix more rapidly thus better preserving polarization during the stage of forming the solution. U.S. Pat. No. 6,466,814 and U.S. Pat. No. 6,278,893 do not teach how to form a suspension, colloid or other type of mixture nor do they describe how to polarize encapsulated material. A further aspect of this disclosure teaches methods for producing these types of mixtures employing hyperpolarized materials.

The present disclosure thus describes a process for manufacturing hyperpolarized solutions in a novel manner; furthermore it teaches the manufacture of hyperpolarized suspensions and/or other mixtures. The disclosed methods do not require the use of adulterating catalysts, which removes the presence of potentially toxic materials and furthermore permits the material to be extracted from the polarizer in the solid state. If desired, the hyperpolarized material may be stored/transported that it may be used at a site remote from the polarizing cryostat, by dissolving or dispersing said material in an appropriate liquid, or combination of liquids, or solutions.

Accordingly, Applicant has developed methods of polarizing materials that do not incorporate a catalyst such as a trityl radical. The method permits materials to be extracted from a polarizing environment while still in the solid state so that they can be stored/transported without excessive polarization loss. The methods further permit the hyperpolarized materials to be rendered in the form of a solution, suspension, encapsulation and the like so that they may be made use of in an in vivo MR study.

When a spin ensemble consisting of spin ½ nuclei (such as $^{13}$C, $^{129}$Xe, $^{15}$N, $^{1}$H, etc.) is placed in an external magnetic field, the interaction of the quantized magnetic moment of the nuclei (m=±½) with the field gives rise to two possible energy states for the system. Typically, these states are labeled "up" (m=½) and "down" (m=−½), referring to whether the magnetic moment of the nuclei is parallel or anti parallel to the ambient magnetic field.

In a non zero magnetic field, the "up" state is a lower energy arrangement than the "down" state. For this reason, in thermodynamic equilibrium, the population of spins in the "up" state will exceed that of the "down" state. The ratio of nuclear spins in the "up" state to those in the "down" state is known as the "Zeeman polarization" or "Boltzmann polarization" of the system; it can be calculated for any temperature T by means of the equation P=tan h μB/kT where μ=the gyromagnetic ratio of the spin and k=Boltzmann's constant. "Hyperpolarization", as described herein, refers to the production of nuclear polarization in excess of thermodynamic equilibrium.

An ensemble of spins that is "hyperpolarized" will seek to relax back to thermodynamic equilibrium. Typically, relaxation is exponential with respect to time, the time constant at which this occurs is known in the art as "$T_1$". In NMR terminology, $T_1$ is the time constant for the recovery of the z component (i.e., $M_z$, which is parallel to the ambient magnetic field) of nuclear magnetization and describes interactions between the spin ensemble and the lattice. Note that $T_1$ is a function not only of the type of nuclei that is hyperpolarized but also be temperature, field, molecular structure, or a combination of all of the above.

Another characteristic time constant of NMR experiments is $T_2$. This is formally known as the time constant for the recovery of the $M_{x,y}$ components of the nuclear magnetization (i.e., perpendicular to the ambient magnetic field) of nuclear magnetization. Less formally, it is the time constant that describes spin-spin interactions and is usually associated with the line width of the NMR signal in Fourier space. Like $T_1$, $T_2$ can also be a function of temperature, field, molecular structure etc. Notably, in a solid, $T_2$ is always less than $T_1$ whereas in a liquid $T_2 \sim T_1$. In a low field thermal mixing experiment, the time for polarization to transfer between nuclei is typically $\sim T_2$. The time for polarization to decay to the lattice entirely is $\sim T_1$. It is therefore important that the time of exposure of a hyperpolarized material to a low magnetic field (to permit thermal mixing of protons in a methyl group with other nuclei (e.g. carbon nuclei of the methyl group)) be $T_2 > t > T_1$.

In accordance with a first exemplary embodiment, a method is provided that first includes the step of configuring a material. The material preferably contains a molecule containing at least one $CH_3$ methyl group and a nuclei with a non zero spin. Preferably the nuclei are of a high $T_1$ material at STP. The method then optionally specifies pelletizing the sample so that it can be rapidly introduced into and extracted from the high B/T environment inside the polarizing cryostat.

Applicant has described in previous applications (e.g., PCT/US2009/39696, filed Apr. 6, 2009) how a liquid may be frozen and pelletized, for example by droppering it into LN2. This has been used to create frozen pellets of glacial acetic acid, for example. A similar process can be used on solutions, emulsions, suspensions etc. Gases may also be pelletized; as a non exclusive example this can be done by freezing them onto the surface of a powder.

Pelletizing molecules that are liquids at room temperature for use in MRI studies have been described in the art. For example U.S. Pat. No. 5,617,859 describes the use of pelletized liquids that can be polarized by subjecting them to a high magnetic field. However, that teaching does not disclose the use of methyl rotors or quantum tunneling based phenomena to rapidly relax one set of nuclei in a very high B/T environment. Nor does it describe the use of low fields to transfer polarization from one nuclei in the molecule to another. Finally it does not teach controlling the temperature/field of the pellet so as to avoid undue relaxation loss during extraction of the pellet from the polarizing environment. These steps, as disclosed herein, are used to manufacture polarized molecules, in particular molecules containing a $CH_3$ methyl group, and incorporating them with a fluid at room temperature so as to form a solution, suspension or other type of mixture.

In accordance with a further aspect, the exemplary method further provides exposing the pellet to a high B/T environment, such as can be produced using a high field superconducting magnet and a low temperature cryostat, for sufficient amounts of time to produce high levels of polarization in at least one nuclear species in the material (in particular, the methyl protons in a $CH_3$ group). The method also provides directing the pellet from the high field region of the magnet such that it is exposed for a brief time to a low magnetic field such as that provided by the Earth's ambient field (~0.5 G) or a shielded container such as mu-metal. The method of expulsion is preferably carried out using helium gas as a propellant and the speed of the pellet is preferably that such that the time of exposure to the low field, t, is $T_2 < t < T_1$.

Applicant has discovered that, at certain temperatures, the relaxation time of a molecule containing a methyl group may be very rapid. These temperatures, known as $T_{min}$, can provide a path for depolarization, if the molecule is allowed to linger at such ambient conditions for too long, and this can become more acute in low fields. The exemplary method thus further provides optionally controlling the temperature of the pellet such that during exposure to the low field environment it is well away from a temperature where its nuclear relaxation time is very fast. For example, the pellet can be warmed to be well above $T_{min}$ and then directed from the high B/T environment.

In a further aspect, the method also can provide that, after expulsion from the high field magnet, the material remains in the solid state. Once outside the polarizing cryostat the pellet can be maintained at a temperature where the $T_1$ of the heteronuclei of interest is of a desired length of time. For example, this can be done by storing the pellet at 4 K and in a magnetic field >0.1 Tesla such as that provided by a permanent magnet. The hyperpolarized material may then be employed immediately or at some future/location to form a solution, suspension, colloid, or other mixture, which can then be used to generate an image, dynamic flow data, diffusion data, perfusion data, physiological data or metabolic data. The following further Examples are similarly based partially on experience and partially on insight.

Example 2

Liquid 1-$^{13}$C labeled acetic acid is frozen into pellets by droppering it into liquid nitrogen ("LN2"). The pellets are collected and introduced into a high B/T environment (such as a cryogenic environment at about 150 mK in a background field of 8-10 Tesla). They are kept in the high B/T environment until the protons in the methyl ("$CH_3$") group in the acetic acid have fully relaxed, this can be observed using NMR or by measuring in advance the proton $T_1$ under such conditions. The pellets are then directed/expelled from the high B/T environment using high pressure helium gas through a conduit. It will be appreciated that the practice of accelerating light frozen pellets is generally well-known, for example, in the field of introducing frozen hydrogen pellets into fusion tokamaks at speeds on the order of 1000 m/second. As they are expelled, the pellets pass out of the polarizing field and into a region of very low field so that polarization flows from the protons to nearby $^{13}$C labeled carbonyls. The pellets are collected in a volume outside the high B/T environment where the ambient temperature/field environment of the pellets can be independently controlled. As a non exclusive example, the volume can be maintained at ~200 K through the use of dry ice. A small permanent magnet can be used to maintain a field on the pellets. Under such conditions the $T_1$ of the $^{13}$C in the acetic acid is on the order of several minutes; long enough to transport the polarized acetic acid a short distance. The pellets can then be melted in the volume and reacted with a warmed buffered solution to produce highly polarized sodium acetate solution.

Example 3

Liquid 1-$^{13}$C acetic acid pellets are manufactured and cooled to high B/T conditions as described in embodiment 1. When the protons in the $CH_3$ group have been polarized, the pellets are warmed while still in the polarizing field to a temperature above $T_{min}$ but still well below their melting temperatures (Tmelt for acetic acid ~17° C.). Then they are directed/expelled from the polarizing cryostat so that they can be collected for storage/transport or melted for immediate use.

Example 4

Powderized anhydrous 1-$^{13}$C labeled sodium acetate is mixed with a suitable solvent for in vivo MR applications such as buffered water or saline. The solution is then frozen into pellets, for example by droppering it into LN2. The pellets are then exposed to a high B/T environment. They are kept in the high B/T environment until the protons in the $CH_3$ group in the sodium acetate have fully relaxed. The pellets are then directed/expelled from the high B/T environment using high pressure helium gas. The pellets can then be melted, for example by mixing them with heated water or saline solution, to produce highly polarized sodium acetate solution.

Example 5

Powderized anhydrous 1-$^{13}$C labeled sodium acetate is mixed with a suitable solvent for in vivo MR applications such as buffered water or saline. The solution is then encapsulated in a thin polymer shell to form individual beads sufficiently small for in vivo applications. The pellets can optionally be functionalized so as to produce a desired in vivo function; for example, to bind to a desired in vivo structure such as a fibroid or tumor. The optionally functionalized capsules are kept in the high B/T environment until the protons in the $CH_3$ group in the sodium acetate have fully relaxed. The pellets are then directed/expelled from the high B/T environment using high pressure helium gas and mixed with a physiologically tolerable solution to form a hyperpolarized suspension.

The disclosure further provides one method of performing NMR spectroscopy. The method includes introducing a hyperpolarized material made in accordance with any of the teachings herein into a region of interest, transmitting a pulse of electromagnetic energy into the region of interest to excite the hyperpolarized encapsulated material, and receiving NMR spectra from the region of interest. Accordingly, the materials provided herein can be used to analyze the NMR spectra of an in vitro or in vivo sample. Moreover, in accordance with a further aspect, it is possible to hyperpolarize a material suitable for being metabolized in a biological process in accordance with any of the teachings herein, introducing the hyperpolarized material into a region of interest; and receiving NMR data or MR images indicative of metabolism of the hyperpolarized material. Such techniques can be useful for diagnosing the existence of particular types of tissues, as set forth in U.S. patent application Ser. No. 12/193,536, filed Aug. 18, 2008, which is incorporated by reference herein in its entirety.

It will also be appreciated by those of skill in the art that the protons in methyl groups as described herein can be polarized in accordance with a variety of techniques, such as (i) by way of a quantum relaxation switch, (ii) dynamic nuclear polarization, (iii) the Nuclear Overhauser effect, (iv) parahydrogen induced polarization, (v) exposing the nuclei of the first material to hyperpolarized nuclei of a previously hyperpolarized gas, (vi) exposing the first material to a brute force environment and combinations thereof.

Dynamic nuclear polarization ("DNP") generally involves transfer of polarization from electron spins to nearby nuclear spins; typically, although not exclusively, via saturation of the electron resonance line using microwave irradiation. An example of DNP in the patent literature includes U.S. Pat. No. 6,008,644 which is incorporated by reference herein in its entirety. In the context of certain of the embodiments of the present disclosure, DNP can be used, for example, to hyperpolarize the protons in the methyl group of a material The Nuclear Overhauser effect generally involves transfer of nuclear polarization from one set of nuclear to spins to another set of nearby nuclear spins; typically, though not exclusively, by saturation of the first set of spins nuclear resonance line. Examples of the Nuclear Overhauser effect in the literature are described in Schlichter, Principles of Magnetic Resonance, 2nd ed. Springer Velas, Berlin, 1978, which is incorporated by reference herein in its entirety. In the context of certain of the embodiments of the present invention, the Nuclear Overhauser effect can be employed by causing the hydrogen nuclei in methyl groups to have a higher than usual polarization.

Parahydrogen induced polarization ("PHIP") can be used to hyperpolarize the hydrogen atoms in methyl groups. PHIP generally involves transfer of polarization via catalyzed hydrogenation by p-$H_2$, followed by spin-order transfer to the nucleus of interest. Examples of PHIP in the patent literature include, for example, U.S. Pat. No. 6,574,495, which is incorporated by reference herein in its entirety.

Brute force hyperpolarization, preferably using a quantum relaxation switch, (referred to herein as "QRS") can be used to hyperpolarize the hydrogen atoms in methyl groups (or other material). As a term in the art, brute force refers to exposing the material to be hyperpolarized to very low temperature, high magnetic field conditions. Materials in a "brute force" environment will tend to naturally relax to a state of high nuclear polarization. However, without use of additional mechanisms, the time to achieve hyperpolarization is generally too long to be of practical use. By using a hyperpolarization facilitator such as $^3$He, a quantum relaxation switch provided by the $^3$He facilitates relaxation of the material under while in brute force conditions to rapidly induce hyperpolarization in the material. Application of $^4$He is then used to remove the $^3$He from the hydrogen atoms in methyl groups to enable it to be warmed to room temperature without undue loss of hyperpolarization. An example of QRS in the patent literature includes U.S. Pat. No. 6,651,459 which is incorporated by reference herein in its entirety.

The hydrogen atoms in methyl groups may also be hyperpolarized by exposing them to hyperpolarized nuclei of a previously hyperpolarized gas. This can be carried out in a variety of ways, such as by immersing the first material in liquefied hyperpolarized $^{129}$Xe, or by allowing gaseous polarized xenon to be bubbled through the material. An example of nuclear hyperpolarization transfer from a gas in the patent literature can be found in U.S. Pat. No. 6,426,058 which is incorporated by reference herein in its entirety.

The "Overhauser effect", is considered to be the transfer of polarization from an electron to a nucleus. As further described herein, the "Nuclear Overhauser Effect" is a similar phenomena, except that the transfer is from one nucleus to another. In each case polarization is transferred from one set of spins (electron—nucleus in the case of the "Overhauser Effect", nuclear—nuclear in the case of the "Nuclear Overhauser Effect"). The techniques may utilize application of radiofrequency ("RF") pulses to the material, or not, depending on whether the two sets of spins (i.e., (i) electron-nucleus or (ii) nucleus-nucleus) are in motion with respect to one another.

The methods and systems of the present disclosure, as described above and shown in the drawings, provide for superior hyperpolarized materials and methods for making the same. All patents, patent applications and references referred to herein are incorporated by reference herein in their entireties. It will be apparent to those skilled in the art that various modifications and variations can be made in the device and method of the disclosed embodiments without departing from the spirit or scope of the disclosed embodiments. Thus, it is intended that the present disclosure include modifications and variations that are within the scope of the subject disclosure and equivalents.

What is claimed is:

1. A process for manufacturing a hyperpolarized material, comprising:
a) providing a first material to be polarized, the first material including a methyl rotor group;
b) increasing the polarization of at least one hydrogen nuclei in the methyl group of the first material by exposing the first material to a polarizing environment inside of a cryostat by (i) decreasing the temperature of the first material, and (ii) subjecting the first material to an increased magnetic field, wherein the first material is exposed to the polarizing environment for a time sufficient to polarize at least one hydrogen nuclei contained in the first material to thermodynamic equilibrium; and
c) transferring at least some of the increased polarization of the at least one hydrogen nuclei to at least one other nuclei in the first material by directing the first material out of the cryostat, through a region of decreased magnetic field on the order of the Earth's background magnetic field to a second location.

2. The method of claim 1, wherein the first material is transferred from the polarizing environment through the region of decreased magnetic field to the second location over a time period greater than $T_2$ but less than $T_1$.

3. The method of claim 2, wherein the first material is transferred from the polarizing environment to the second location in less than 1.0 second.

4. The method of claim 1, wherein the first material is isotopically enhanced by substituting one or more of its atomic sites with at least one of $^{129}Xe$, $^{13}C$, $^{15}N$, $^{1}H$, $^{2}H$, $^{31}P$, $^{19}F$ and $^{29}Si$.

5. The method of claim 1, wherein the first material has been substantially purged of paramagnetic agents and polarization agents prior to polarization.

6. The method of claim 1, wherein increasing the polarization of the first material is facilitated by contacting the first material with $^{3}He$.

7. The method of claim 1, wherein the first material is a liquid at STP.

8. The method of claim 1, wherein the magnetic field strength in the region of decreased magnetic field is lower than the Earth's background magnetic field.

9. The method of claim 1, wherein the second location includes a transport cryostat including a magnet, wherein the magnet applies a magnetic field to the first material at a low temperature.

10. The method of claim 1, wherein the first material is in a solid state after the polarization step and after the first material is directed to the second location by accelerating it with fluid pressure.

11. The method of claim 10, wherein the first material is directed to the second location by directing it through a conduit with a compressed gas.

12. The method of claim 1, further comprising warming the first material from below the temperature at which the T1 of the first material experiences a minimum ($T_{min}$) to a second temperature above the temperature at which the $T_1$ of the first material experiences a minimum ($T_{min}$) without substantially melting or sublimating the first material.

13. The method of claim 1, further comprising mixing the first material with a second material to form a solution after the transferring step.

14. The method of claim 1, wherein the first material includes pyruvic acid.

15. The method of claim 1, wherein the first material includes acetic acid.

16. The method of claim 1, wherein polarization is achieved in step (b) at least in part by a brute force technique without the addition of a polarizing agent or an externally added relaxation agent.

17. The method of claim 1, wherein polarization is transferred in step (c) from the at least one hydrogen nuclei to a carbon atom.

18. The method of claim 17, wherein the carbon atom is in the methyl group.

19. A process for manufacturing a hyperpolarized material, comprising:
 a) providing a first material to be polarized including pyruvic acid, the pyruvic acid including a methyl rotor group;
 b) increasing the polarization of at least one hydrogen nuclei in the methyl group of the first material in a polarizing environment using a brute force technique without the addition of a polarizing agent or an externally added relaxation agent;
 c) transferring at least some of the increased polarization of the at least one hydrogen nuclei to at least one carbon nuclei in the methyl rotor group of the pyruvic acid by way of thermal mixing in an environment external to the polarizing environment having a magnetic field on the order of Earth's background magnetic field; and
 d) directing the first material to a second location.

20. The method of claim 19, further comprising the step of transporting the first material to a location within the fringe field of an MR system.

21. The method of claim 19, further comprising increasing the temperature of the first material from a first temperature below the temperature at which the $T_1$ of the first material experiences a minimum ($T_{min}$) to a second temperature above $T_{min}$ without melting or sublimating the first material.

22. The method of claim 21, wherein the temperature is increased from the first temperature below $T_{min}$ to the second temperature above $T_{min}$ while the first material is situated in the transport cryostat.

23. The method of claim 21, wherein the temperature is increased from the first temperature below $T_{min}$ to the second temperature above $T_{min}$ while the first material is being directed into a transfer vessel.

* * * * *